United States Patent [19]

Whitney et al.

[11] 4,267,836

[45] May 19, 1981

[54] INJECTION DEVICE AND METHOD

[76] Inventors: Douglass G. Whitney, 2518 W. Wesley Rd.; John K. Martin, III, 2837 Ridge Wood Cir., both of, Atlanta, Ga. 30327

[21] Appl. No.: 30,277

[22] Filed: Apr. 16, 1979

Related U.S. Application Data

[62] Division of Ser. No. 471,528, Nov. 12, 1976, Pat. No. 4,150,672.

[51] Int. Cl.³ .............................................. A61M 5/20
[52] U.S. Cl. ................................. 128/215; 128/218 F
[58] Field of Search ............... 128/214 F, 218 A, 215, 128/218 D, 218 F

[56] References Cited

U.S. PATENT DOCUMENTS

| | | | |
|---|---|---|---|
| 2,413,303 | 12/1946 | Folkman | 128/215 |
| 2,459,875 | 1/1949 | Folkman | 128/215 |
| 2,605,765 | 8/1952 | Kollsman | 128/218 F |
| 2,627,270 | 2/1953 | Glass | 128/218 A |
| 3,141,583 | 7/1964 | Mapel et al. | 128/218 D |
| 3,451,393 | 6/1969 | Sarnoff | 128/214 F |
| 3,640,277 | 2/1972 | Adelberg | 128/214 F |
| 3,880,163 | 4/1975 | Ritterskamp | 128/218 F |
| 3,931,815 | 1/1976 | Takatsuki | 128/218 D |

*Primary Examiner*—Dalton L. Truluck
*Attorney, Agent, or Firm*—B. J. Powell

[57] ABSTRACT

Method and apparatus for injecting fluids into patients at a controlled rate from an ampule with a tubular side wall closed at one end with a penetrable plug and a sliding piston in the side wall to force the fluid through an opening in the penetrable member using either a long duration injector with an expelling means to move the ampule piston, drive means for operating the expelling means, and control means for incrementally and successively connecting and disconnecting the drive means to the expelling means or a short duration injector with a spring drive or a fluid pressure drive to move the ampule piston and meter the fluid through a metering device.

6 Claims, 24 Drawing Figures

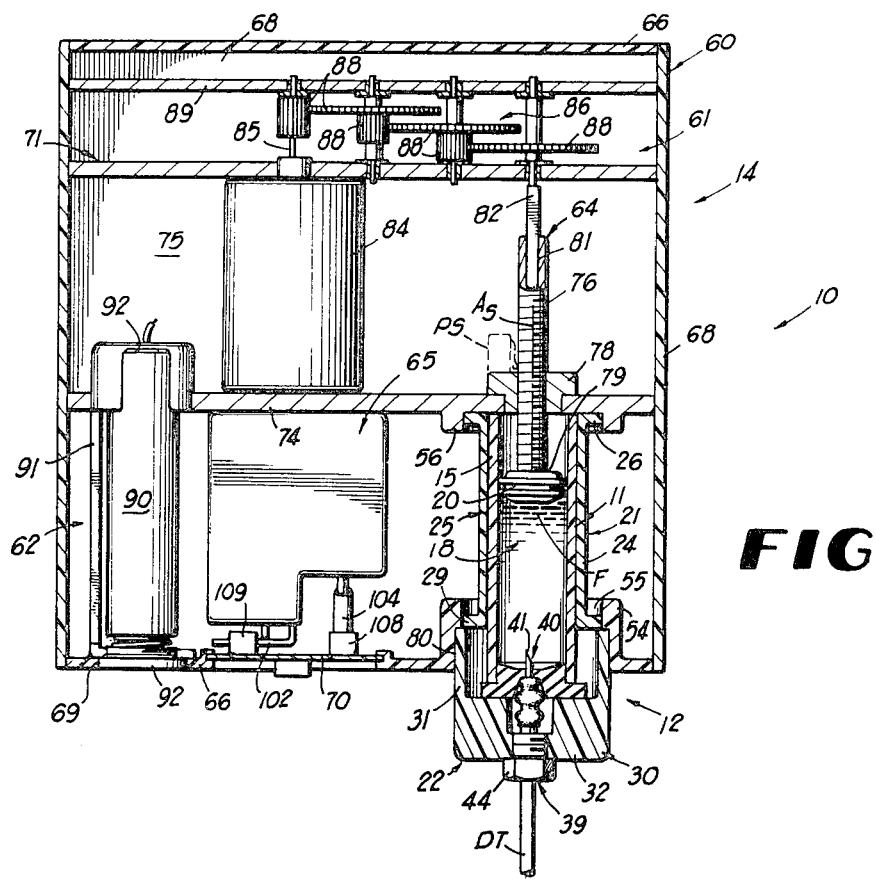
FIG 4
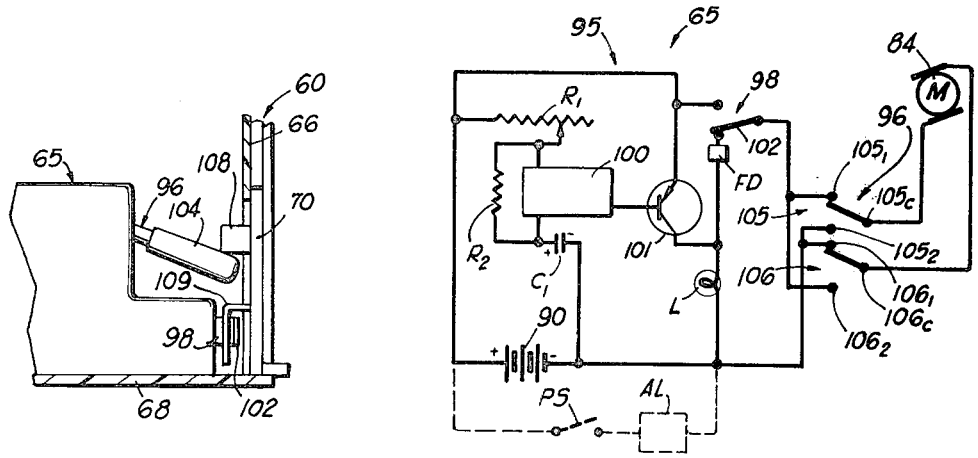
FIG 7
FIG 8

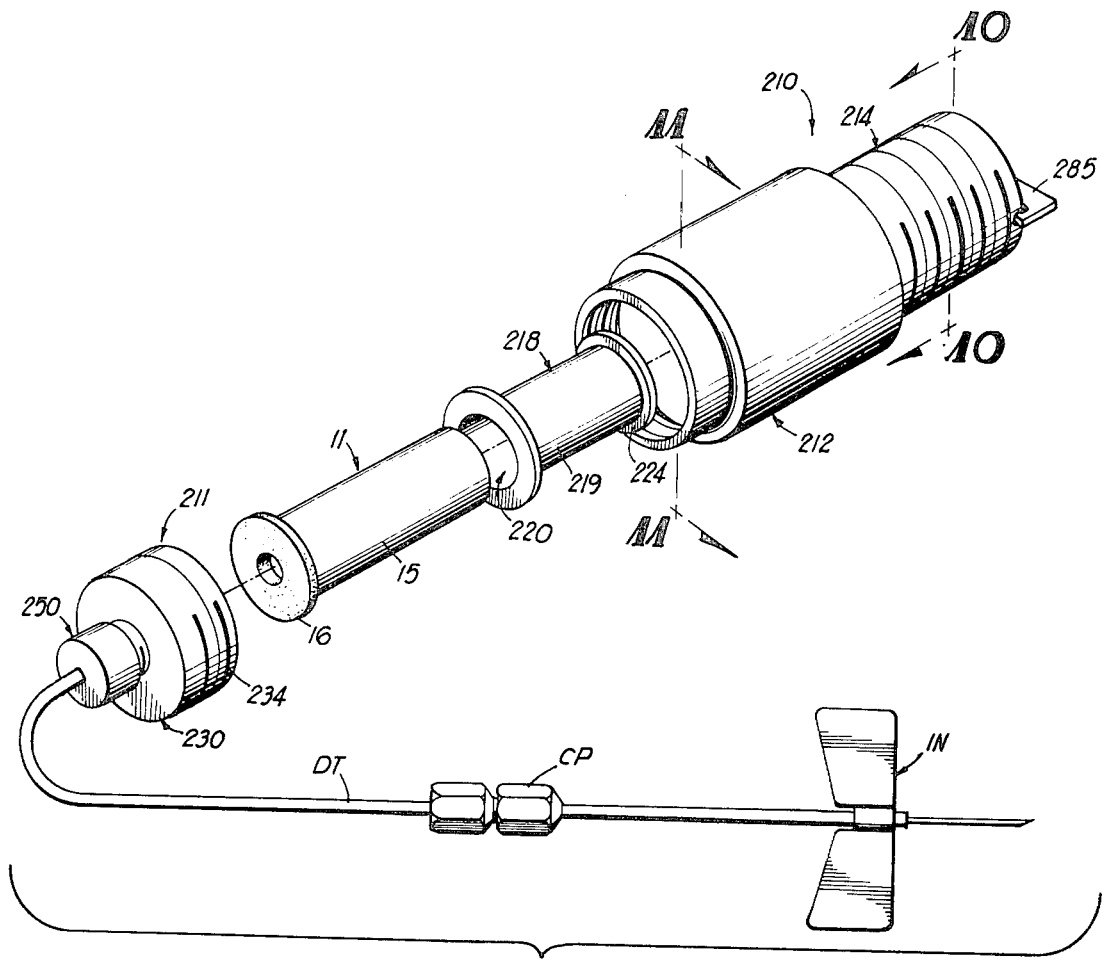
FIG 9
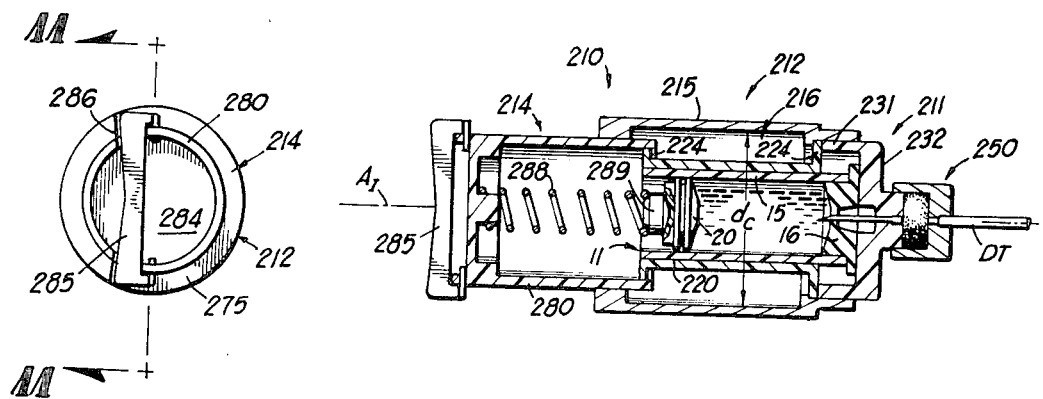
FIG 10
FIG 11

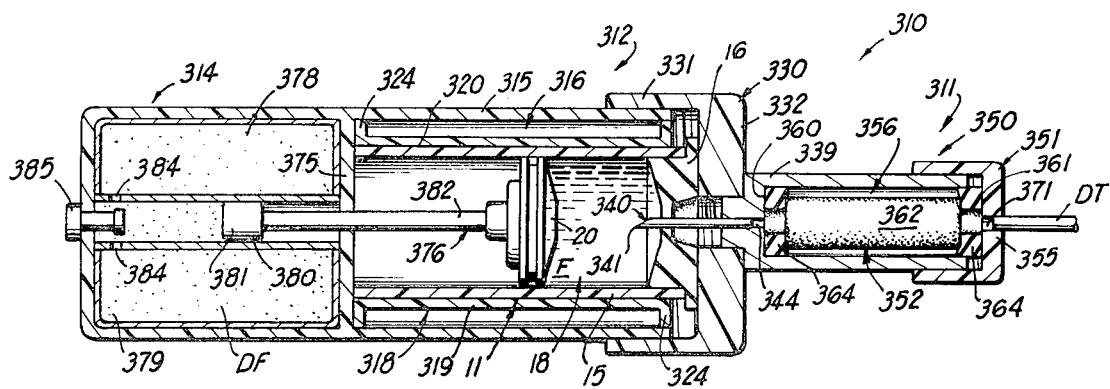
FIG 20
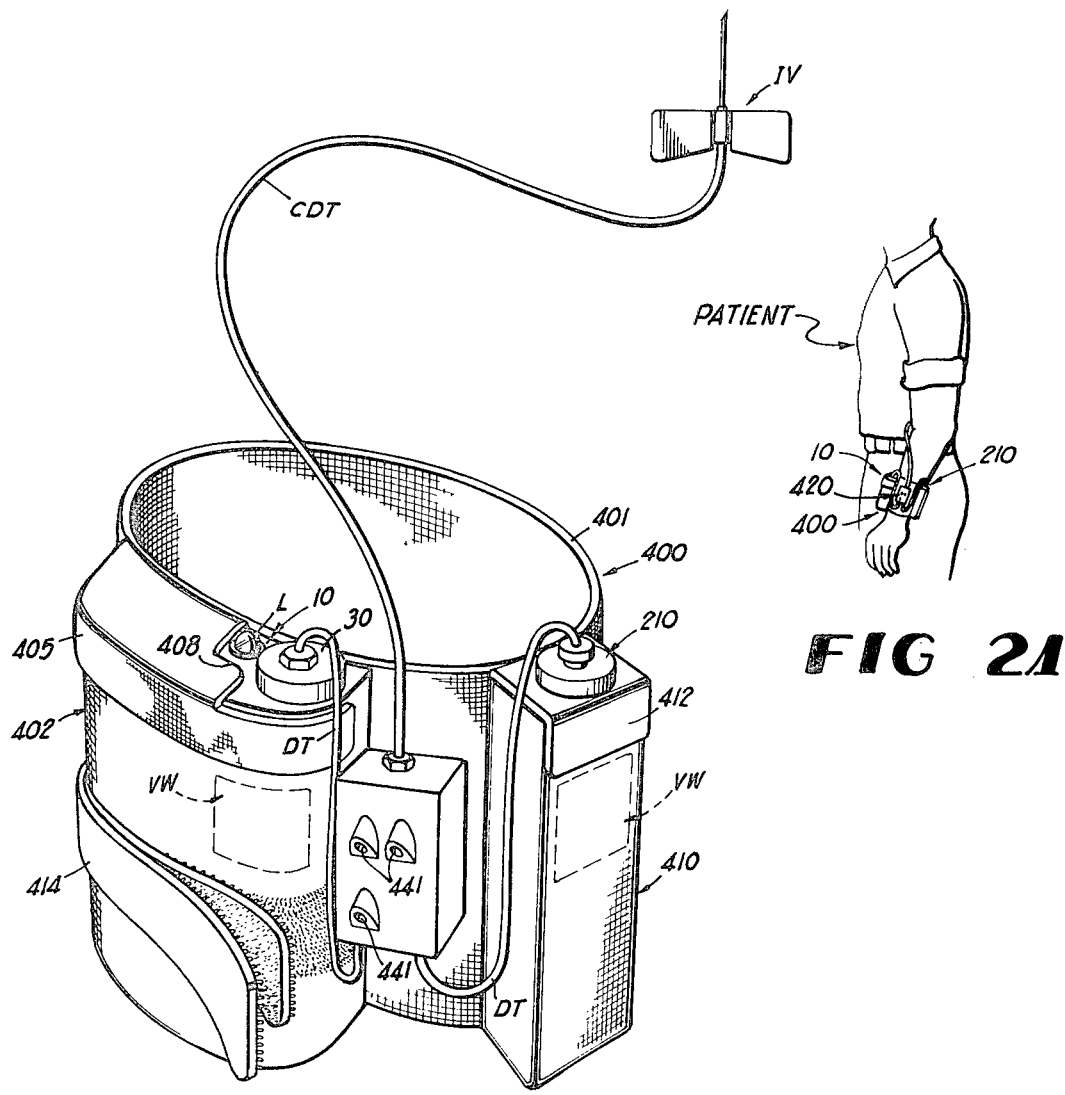
FIG 21
FIG 22

INJECTION DEVICE AND METHOD

This is a division of application Ser. No. 471,528, filed Nov. 12, 1976, now U.S. Pat. No. 4,150,672.

BACKGROUND OF THE INVENTION

This invention relates generally to devices for dispensing or injecting a fluid at a controlled rate and more particularly to a device for use in the medical field to inject fluids into the body of a patient at a slow rate over a prolonged period of time.

It is desirable in the medical profession to inject fluids such as liquid medicaments into the body of the patient, whether human or animal, at a relatively slow rate over a prolonged period of time. A wide variety of medical treatments require this low rate of injection such as chemotherapy, pre and post surgery treatments for the prevention of blood clotting, various nutrient treatments, various antibiotic treatments and treatment of certain other diseases. Such injections are generally made intravenously or subcutaneously into the patient. Some of these treatments generally require that the fluid be introduced relatively continuously over an extended period of time at a very slow rate, usually in a range varying from less than 1 cc per 24 hour period to move than 5 cc per 24 hour period. Because a significant increase in the predetermined rate of injection during these continuous treatments must be accurately controlled to prevent serious injury or fatality of the patient, the rate of injection must be frequently and closely monitored. Some of these treatments, on the other hand, require that the treatment fluid be injected over a relatively short period of time at a controlled rate in order to gain the peaking benefit of the treatment fluid.

There are a number of liquid dispensing or injection devices presently known which attempt to dispense or inject a liquid into a patient at a very low continuous rate over an extended period of time. A representative sampling of such devices are disclosed in U.S. Pat. Nos. 3,468,308; 3,469,578; 3,486,539; 3,850,348; and 3,868,973. The devices disclosed in these patents rely generally on some pressure producing driving mechanism which constantly tries to force a quantity of liquid into the patient through an appropriate injection device such as a needle. The rate at which the fluid or liquid is injected is controlled by some type of metering device positioned downstream of the container carrying the liquid to be dispensed and through which the liquid to be dispensed must flow before it reaches the patient. One of the problems with such devices is that a failure of the metering device may result in the flow of liquid into the patient being uncontrolled thereby significantly increasing the rate of injection of the fluid into the patient which can result in serious injury or fatality to the patient. Another problem associated with these prior art devices is that because the flow of liquid from the container into the patient is continuous, it is difficult, if not virtually impossible, to accurately and frequently monitor the flow rate of the liquid into the patient. Furthermore, even though the flow rate of the liquid into the patient may be monitored, the complexity of the monitoring technique requires that the patient remain in a confined setting with appropriate qualified medical personnel available to monitor the flow rate. This not only maintains the cost of delivery of the services necessary to dispense or inject the liquid into the patient at a very high level but also seriously limits the patient's ambulatory capability thereby resulting in loss of productive time of the patient. While it is frequently necessary to change the rate of injection of the liquid into the patient during the treatment process, most prior art devices do not have the capability of readily changing the injection rate and/or require that the device be removed from the patient for adjustment or change of injection rate. These prior art devices generally require skilled medical personnel to change the injection rate and also increase the likelihood of infection for the patient.

SUMMARY OF THE INVENTION

These and other problems and disadvantages associated with the prior art are overcome by providing an injection device which has the capability of injecting fluid slowly and precisely into a patient at a known, easily measurable and easily variable rate. The device further is extremely fail-safe in that failure of any part of the device will result in disabling the device to prevent a too rapid injection rate or any further injection of the fluid. Further, the device provides a human receptive indicator, visable and/or audible, of whether the device is working which can be easily and readily monitored by the patient and/or medical personnel thereby greatly reducing the number and skill of medical personnel necessary to monitor the injection rate. Further, the device of the invention is easily and highly portable so that the patient is not hampered in his ambulatory capability thereby maximizing the amount of productive time available to the patient even during treatment. Because of these features, the device is ideally suited for out-patient use not presently clinically available thus preventing unnecessary hospitalization and expense. Further, the device of the invention provides sufficient accuracy and safety in operation to assure that the proper injection rate is maintained. The device also has the capability of selectively flushing the tubing connecting the device to the patient allowing for rapid preparation and further has the capability of preventing operation of the flushing mechanism while the device is in its normal injection operation to prevent injury to the patient. The invention also has the capability of not only injecting a treatment fluid at a relatively slow average rate over a prolonged period of time but also at a continuous rate over a relatively short period of time. Also, the device is extremely simple in construction and operation thereby making it sufficiently inexpensive to be disposed of after each patient use to reduce not only the cost of delivery to the patient from a control standpoint but also from a confinement standpoint.

One embodiment of the invention is an intermittent injection device which includes generally a container for the fluid to be injected in a sterile condition and defining an outlet from which the fluid is to be injected which is connected via tubing to the patient, an expelling mechanism which is operatively associated with the fluid in the container to forcably expel the fluid from the container through the outlet for injection when the expelling means is driven, a driving mechanism for selectively driving the expelling mechanism to force the fluid from the container, and a control means for selectively connecting and disconnecting the driving means to the expelling means to incrementally and successively drive the expelling means to successively and incrementally expel the fluid from the container at an average prescribed rate over a prescribed period of time. Because the fluid is injected incrementally, monitoring is greatly simplified and precise.

The expelling mechanism may include a drive screw which forces the fluid from the ampule as it is rotated and a drive motor for directly or indirectly rotating the drive screw when it is driven. The driving means may include an electrical power supply and the control means may include a timed switching circuit which selectively and alternatively connects and disconnects the electrical power supply to the drive motor to successively and incrementally drive the motor and thus the drive screw. The time period that the power supply is disconnected from the drive motor may be selectively varied while the time period that the power supply is connected to the drive motor is left relatively constant so that the overall injection rate can be readily varied and the injection rate can be easily monitored by noting the frequency of the drive pulses.

Another embodiment of the invention is a continuous injection device which includes generally a container for the fluid to be injected in a sterile condition and defining an outlet from which the fluid is to be injected via tubing to the patient, an expelling mechanism which is operatively associated with the fluid in the container to forcibly expel the fluid from the container through the outlet, and a flow control mechanism connected to the outlet of the container for controlling the flow rate of the fluid being injected into the patient. The flow control mechanism includes means for allowing the tubing to be flushed in a first position and for accurately metering the flow rate in a second position.

The container for either of the above injection devices may include an ampule with a seamless tubular side wall defining a passage therethrough which is closed at one end by a penetrable member so that the discharge opening may be made by penetrating the penetrable member. A piston member is slidably received in the passage to define a closed fluid chamber in the ampule whereby movement of the piston member will cause the fluid to be dispensed from the fluid chamber upon penetration of the penetrable member and movement of the piston member toward the penetrable member. The ampule may have means incorporated therein to insure proper orientation of the ampule. The penetrable member is usually penetrated by a piercing needle and the piercing needle may be enclosed by positioning means and a penetrable cover member that can be penetrated by the needle with means for urging the penetrable cover over the piercing end of the needle to enhance the sterility of the piercing needle.

The invention also includes a method of injecting a fluid into a patient at an average prescribed rate over a prolonged period of time which includes alternatively injecting the fluid into the patient at a first rate greater than the average prescribed rate for a first short period of time and alternatively stopping the injection of the fluid into the patient for a second short period of time so that the fluid is injected into the patient at the desired average prescribed rate over the sum of the first and second short periods of time. The method may also include selectively varying the second period of time to selectively change that average prescribed rate of injection as well as providing a human receptive indication of each occurrence of the injection during the first period of time.

These and other features and advantages of the invention disclosed herein become more apparent upon consideration of the following detailed description and accompanying drawings wherein like characters of reference designate corresponding parts throughout the several views and in which:

BRIEF DESCRIPTION OF THE DRAWINGS

FIG. 4 is an enlarged cross-sectional view taken generally along line 3—3 in FIG. 1 with the ampule in operative position;

FIG. 7 is a cross-sectional view taken along line 7—7 in FIG. 1;

FIG. 8 is an electrical schematic view showing an embodiment of the control circuit of the invention of FIG. 1;

FIG. 9 is an exploded perspective view of a second embodiment of the invention;

FIG. 10 is an enlarged end view taken along line 10—10 in FIG. 9 showing the expelling mechanism in its locked driving position;

FIG. 11 is an enlarged longitudinal cross-section taken along line 11—11 in FIGS. 9 and 10 showing the invention assembled;

FIG. 20 is a view similar to FIG. 19 showing the invention in use;

FIG. 21 is a reduced perspective view showing the invention in use on a patient;

FIG. 22 is a perspective view showing the support harness of the invention;

Figure 1:
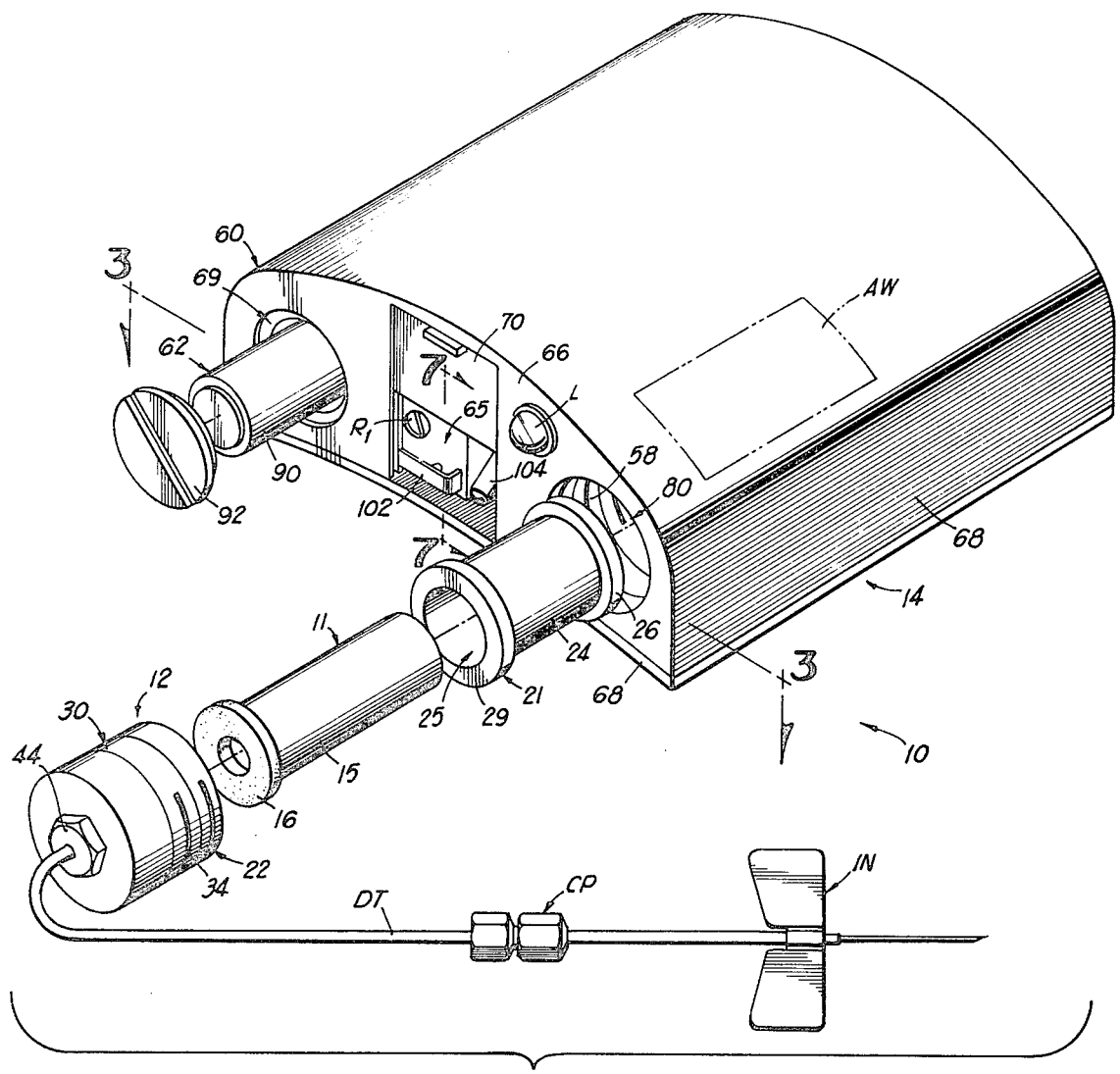
FIG. 1 is an exploded perspective view illustrating one embodiment of the invention.

These figures and the following detailed description disclose specific embodiments of the invention, however, it is to be understood that the inventive concept is not limited thereto since it may be embodied in other forms.

DETAILED DESCRIPTION OF ILLUSTRATIVE EMBODIMENTS

Referring to FIGS. 1–8, it will be seen that the first embodiment of the dispensing and injecting device 10 includes generally a fluid ampule or container 11, an ampule support and connector unit 12, and a power unit 14. The ampule support and connector unit 12 mounts the ampule 11 on the power unit 14 so that the power unit 14 forces the fluid from the ampule 11 to the patient through the ampule support and connecting unit 12.

Figure 2:
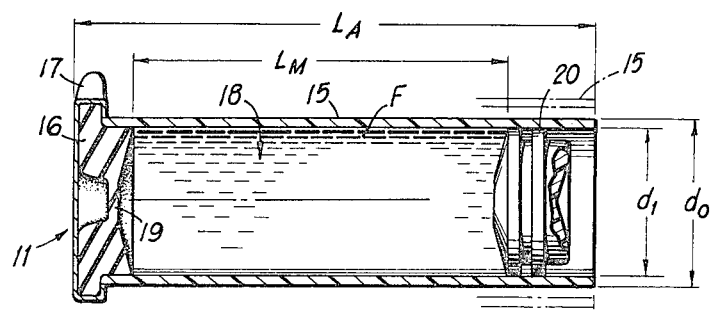
FIG. 2 is an enlarged longitudinal cross-sectional view of the ampule of the invention.

The ampule 11 seen in FIGS. 1, 2 and 4 includes generally a tubular side wall 15 closed at one end by a penetrable rubber plug 16 to define a fluid chamber 18 therein which is open at that end of the side wall 15 opposite the rubber plug 16. The rubber plug 16 may be provided with a thinner central needle penetrating portion 19 to facilitate the penetration thereof as will become more apparent. The opening to the fluid chamber 18 is closed by a slidable piston 20 which slidably engages the side wall 15 in a sealing relationship therewith to hold the fluid F to be injected in the fluid chamber 18. Thus, it will be seen that when the rubber plug 16 is pierced to form a fluid outlet opening therethrough, the fluid F carried in the chamber 18 may be expelled through the pierced opening in the plug 16 by forcing the piston 20 into the side wall 15. The leading side of piston 20 is complimentarily shaped to the inboard side of plug 16 to insure complete expulsion of the fluid from chamber 18. The leading portion of the piston 20 may also be penetrable as will become more apparent.

The usable volume of the ampule 11 is controlled by the maximum usable length $L_M$ of the fluid chamber 18 as seen in FIG. 2 where the piston 20 is adjacent the open end of chamber 18 and the diameter $d_1$ of the fluid chamber 18. Because it is desirable to keep the overall length $L_A$ (FIG. 2) of the ampule 11 generally fixed as will become more apparent, the usable volume of the fluid chamber 18 can be changed by changing the diameter $d_1$. This will also vary the outside diameter $d_o$ of the side wall 15 as seen in FIG. 2 by phantom lines.

The penetrable rubber plug 16 may be covered by a tear-off cover member 17 as seen in FIG. 2 to insure sterility of the plug 16. Because the fluid chamber 18 is completely enclosed by plug 16, side wall 15 and piston 20, the sterility of the fluid F is maintained prior to use. The rubber plug 16 may have an outside diameter larger than the outside diameter $d_o$ of ampule side wall 15 to prevent the ampule from being inadvertently reversed when it is installed as will become more apparent.

The ampule support and connecting unit 12 seen in FIGS. 1 and 3–6 includes generally an ampule support 21 and a piercing cap assembly 22. The ampule support 21 locates the ampule 11 on the power unit 14 while the piercing cap assembly 22 locks the ampule 11 in place and pierces the penetrable section 19 in the ampule rubber plug 16 to connect the fluid in the ampule 11 to appropriate delivery tubing DT. The tubing DT with a coupling CP delivers the fluid to the point of injection into the patient through an appropriate injection needle assembly IN (FIG. 1), usually of the intravenous or subcutaneous type.

Figure 3:
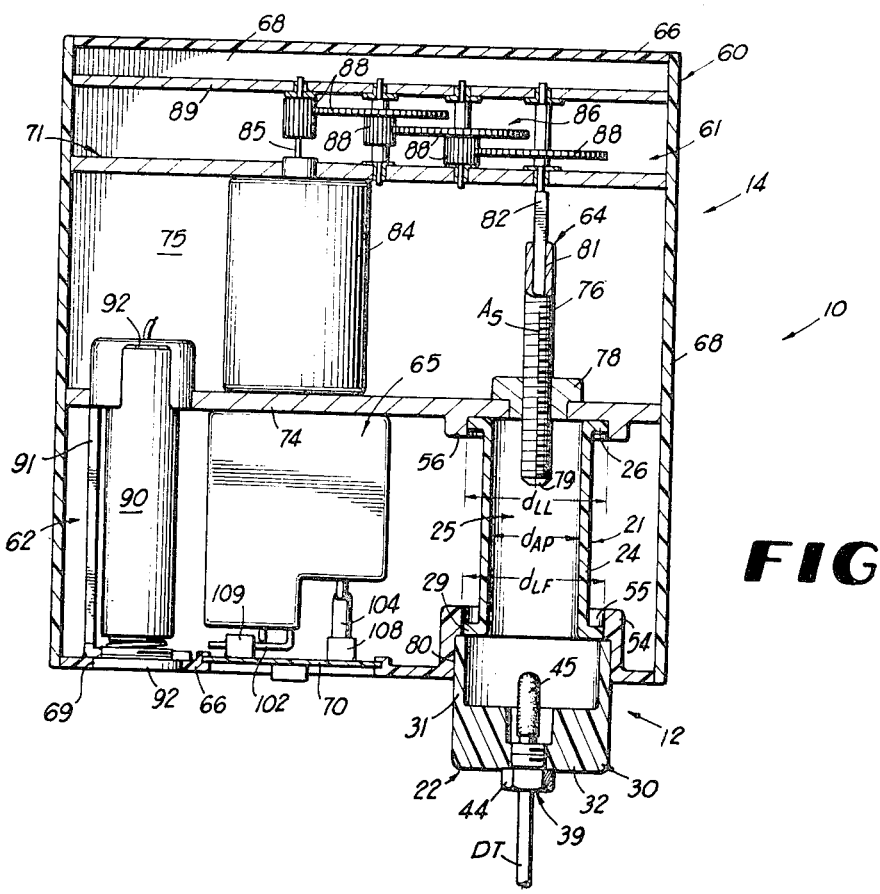
FIG. 3 is a cross-sectional view taken along line 3—3 in FIG. 1 with the ampule omitted.
Figure 5:
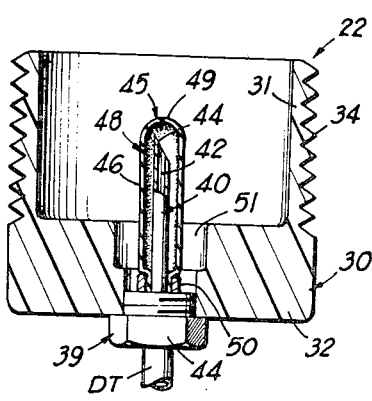
FIG. 5 is an enlarged longitudinal cross-sectional view of the ampule support showing the piercing needle assembly.
Figure 6:
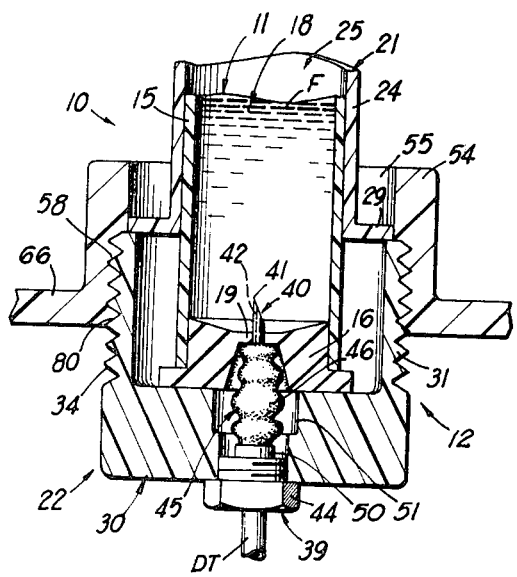
FIG. 6 is an enlarged view similar to FIG. 5 showing the ampule support carrying the ampule.

The ampule support 21 is best seen in FIGS. 3–5 and serves to locate a particular size ampule 11 on the power unit 14. It will thus be seen that a different size ampule support 21 would be used with different diameter ampules 11 as will become more apparent. The support 21 includes a cylindrical side wall 24 which defines an ampule receiving passage 25 therein of diameter $d_{AP}$ (FIG. 3) just large enough to slidably receive the side wall 15 of ampule 11 therein as seen in FIG. 4. The inboard end of the support side wall 24 is provided with an annular, outwardly directed locating lip 26. The lip 26 has an outside diameter $d_{LL}$ larger than the diameter $d_{AP}$. The lip 26 serves to locate the inboard end of the support 21 as seen in FIGS. 3 and 4 on the power unit 14 as will become more apparent. An annular, outwardly projecting locating flange 29 is provided on support side wall 24 adjacent the outboard end thereof as seen in FIG. 3. The flange 29 has an outside diameter $d_{LF}$ which serves to locate the outboard end of support 21 on the power unit 14 as will become more apparent. It will be noted that the length of the support 21 is less than the length $L_A$ of the ampule 11 so that the rubber plug end of ampule 11 projects from the support 21 when it is in position as seen in FIGS. 4 and 6 as will become more apparent. The diameter $d_{LL}$ of lip 26 on the inboard end of support 21 and the outside diameter $d_{LF}$ of flange 29 on the outboard end of support 21 are of a standard fixed size while the diameter $d_{AP}$ of the passage 25 in support 21 may be varied for different diameter ampules 11. Usually, the ampules 11 will be color coded to match that of the proper size support 21 to facilitate assembly. If the ampule 11 to be used will be of a fixed diameter, the support 21 may be built into the power unit 14.

The piercing cap assembly 22 is adapted to be removably attached to the power unit 14 over the rubber plug end of the ampule 11 carried by support 21. The piercing cap assembly includes a cap 30 with a cylindrical tubular side wall 31 closed at its outboard end by a circular end wall 32 seen in FIG. 5. The rubber plug end of ampule 11 is received through the inboard end of the cap side wall 31 until the rubber plug 16 is engaged by the cap end wall 32 as seen in FIGS. 4 and 6. The inboard end of cap side wall 31 is provided with external threads 34 (FIG. 1) which serve to removably connect the cap 30 to the power unit 14 as will become more apparent. The inside diameter of the cap side wall 31 is sized to receive the largest diameter ampule 11 to be used therein.

The piercing cap assembly 22 seen in FIGS. 5 and 6 also includes a piercing needle assembly 39 mounted in the cap wall 32 of cap 30 centrally thereof. The piercing needle assembly 39 includes a tubular piercing needle 40 with a sharpened operating end 41 to pierce the penetrable thin portion 19 in plug 16 of ampule 11 and defines a passage 42 therethrough opening onto the operating end thereof. Thus, when the sharpened end 41 of needle 40 penetrates the portion 19 of plug 16 as seen in FIGS. 4 and 6, the passage 42 serves as a fluid outlet opening to the fluid chamber 18 in ampule 11. The piercing needle 40 may be mounted directly in the cap end wall 32 or through an appropriate connector 44 seen in FIG. 5. The needle 40 projects into the distal end of the ampule chamber 18 sufficiently for the sharpened end 41 of needle 40 to penetrate the penetrable portion in plug 16 when the cap 30 is seated on power unit 14 to place the passage 42 through needle 40 in communication with the fluid chamber 18 in ampule 11 as seen in FIG. 6. It will also be noted that the net inside length of the cap side wall 31 is sufficiently greater than the distance the needle 40 projects inboard of cap end wall 32 so that the threads 34 on cap 30 will engage power unit 14 before the operating end 41 of needle 40 engages the penetrable portion 19 in ampule plug 16. This insures that the needle 40 will not be contaminated when the ampule is installed and also insures that the operating end 41 of needle 40 will be centered on the penetrable portion 19 in the ampule plug 16.

To further enhance the sterility of the needle 40, a cover assembly 45 may be provided over the operating end 41 of needle 40 as seen in FIGS. 5 and 6. The cover assembly 45 must be retractable to expose the needle 40 for use but should automatically cover the operating end 41 of needle 40 when it is not in use. While different configurations may be used, the cover assembly 45 illustrated in FIGS. 5 and 6 includes a resilient tubular side wall 46 defining a needle passage 48 therein. One end of the needle passage 48 is closed by a penetrable end wall 49. The cover assembly 45 has an effective undeformed length such that the open end of the side wall 46 can be slipped over the exposed portion of piercing needle 40 in the cap 30 as seen in FIG. 5 and clamped onto the needle 40 as illustrated by band 50. The operating end 41 of needle 40 will be located in passage 48 behind end wall 49 when the side wall 46 is undeformed. The passage 48 is maintained in a sterile condition. When the cap 30 is installed over ampule 11, the plug 16 will be engaged by the end wall 49 in cover assembly 45 to force the sharpened end 41 of needle 40 through the end wall 49 of cover assembly 45 and then through the penetrable portion 19 in the ampule plug 16. The side wall 46 is now deformed as seen in FIG. 6 to maintain the sterility in passage 48. When the cap 30 is removed from over ampule 11, the natural resiliency of the side wall 46 forces the end wall 49 back over the end 41 of needle 40 so that it returns to passage 48 in cover assembly 45. Thus, it will be seen that the side wall 46 serves a two-fold purpose, first as a means to movably support the end wall 49 coaxially with the sharpened end 41 of the needle 40 and second as a means for urging the end wall 49 from penetration by needle 40. To insure sufficient room for the deformation of the cover assembly 45 a clearance recess 51 may be provided in the cap end wall 32 about the needle 40.

The power unit 14 as seen in FIGS. 1 and 3 includes generally a drive housing 60 which mounts an expelling unit 61 therein to engage the piston 20 in the ampule 11 when the ampule 11 is connected to the power unit 14 through the ampule support and connector unit 12, a drive unit 62 which operates the expelling unit 61, and a control unit 65 which controls the connection of the drive unit 62 to the expelling unit 61. The drive housing 60 is shaped to conform to a portion of the patient's body and has end walls 66 and side walls 68. One end wall 66 is provided with an appropriate closable battery access opening 69 and a control access door 70 as will become more apparent. The end wall 66 is also provided with an ampule opening 80 so that the expelling unit 61 can engage the ampule piston 20 as will become more apparent.

The expelling unit 61 as best seen in FIGS. 3 and 4 is mounted on the drive housing 60 by a generally U-shaped support frame 71. The support frame 71 has upper and lower legs 72 and 74 joined by a central web 75. The expelling unit 61 includes generally a drive screw assembly 64 which engages the piston 20 in the ampule 11, an electrical drive motor 84, and a gear reducer transmission 86 which connects the drive motor 84 to the drive screw assembly 64.

The drive screw assembly 64 (FIG. 3) includes an externally threaded drive screw 76 which is threadedly received in an internally threaded positioning member 78 fixedly mounted on the lower leg 74 of the support frame 71 about a screw axis $A_S$. Thus, it will be seen that, as the drive screw 76 is rotated, it will be threadedly moved axially with respect to the internally threaded positioning member 78. The drive screw 76 has a projecting end 79 which engages the drive piston 20 in the ampule 11 in a self-centering manner as will become more apparent. The drive screw 76 is provided with a non-circular drive passage 81 partly seen in FIG. 3 which slidably receives a complimentary non-circular drive shaft 82 therein from the inboard end of the drive screw 76 so that the drive shaft 82 is coaxially aligned with the drive screw 76 about the screw axis $A_S$. The inboard end of the drive shaft 82 is rotatably mounted through the upper leg 72 of the support frame 71 and is axially fixed relative to the upper leg 72 so that, as the drive shaft 82 is rotated, the non-circular shape of the drive passage 81 in the drive screw 76 and the complimentary non-circular shape of the drive shaft 82 will force the drive screw 76 to be rotated while the drive screw 76 can axially move with respect to the drive shaft 82 as it is axially moved by the positioning member 78.

The drive motor 84 is mounted between the upper and lower legs 72 and 74 of the support frame 71 so that the motor drive shaft 85 projects through the upper leg 72 in frame 71 in general lateral alignment with and parallel to the screw drive shaft 82. The motor drive shaft 85 is connected to the screw drive shaft 82 through the transmission 86. The motor 84 illustrated is a direct current motor. The transmission 86 may have different configurations but is illustrated as including a plurality of intermeshing transmission gears 88, one of which is mounted on the motor drive shaft 85 and one of which is mounted on the screw drive shaft 82 so that the motor drive shaft 85 drives the screw drive shaft 82 through the transmission gears 88. The transmission gears 88 serve as a gear reducer so that the drive motor 84 rotates at a higher rate of speed than the screw drive shaft 82. While the overall gear ratio of the transmission gears 88 may be varied depending on the particular rate at which the drive screw 76 is to be rotated, the gear ratio illustrated as about 216:1 so that the motor turns 216 revolutions for each revolution of the screw drive shaft 82 and drive screw 76. The net axial movement of the drive screw 76 per each revolution of motor 84 is also dependent on the pitch of the threads on drive screw 76. While the pitch may be varied to achieve the desired net axial movement, the drive screw 76 illustrated has 12.6 threads/cm (32 threads/inch) thus producing about 0.8 mm per revolution of drive screw 76 or about 0.0037 mm per revolution of motor 84. The transmission gears 88 between the gear 88 on the motor drive shaft 85 and the screw drive shaft 82 are rotatably journalled between the upper leg 72 of the support frame 71 and an appropriate backup plate 89 for support. Thus, it will be seen that as the drive motor 84 rotates the motor drive shaft 85 in a first direction, the drive screw 76 will be axially moved into engagement with the piston 20 in the ampule 11 to force the fluid out of the ampule 11. On the other hand, reversal of the motor 84 will retract the drive screw 76. It will also be noted that there is no positive connection between the projecting end 79 of drive screw 76 and the piston 20 in ampule 11 so that drive screw 76 can only force the piston 20 toward the plug 16 to force the fluid F out of the ampule 11. Thus, if the drive motor 84 is inadvertently reversed, the screw 76 will retract but the piston 20 will not be moved to prevent the inadvertent extraction of body fluids from the patient.

The ampule support 21 is slidably inserted into housing 60 through the ampule opening 80 as seen in FIG. 1. A locating boss 54 is mounted on the inside of end wall 66 about the ampule opening 80 as seen in FIGS. 3 and 6 with a locating passage 55 therethrough concentric about the screw axis $A_S$. The diameter of passage 55 is just sufficient to slidably receive the flange 29 on support 21 in passage 55 as seen in FIGS. 3 and 6. An annular locating abuttment 56 (FIG. 3) is provided on the outboard side of lower leg 74 of frame 71 about the drive screw 76 with an inside diameter just sufficient for abuttment 56 to receive lip 26 at the inboard end of support 21 therein to locate the inboard end of support 21 concentric about the screw axis $A_S$. Thus, the ampule support 21 is positively located by boss 54 and abuttment 56 concentric about the screw axis $A_S$ so that the ampule 11 will be concentric to axis $A_S$ when placed in support 21. The boss 54 is provided with internal threads 58 at its outboard end as seen in FIG. 1 which are engaged by the cap threads 34 to hold the cap 30 in place.

The drive unit 62 includes a battery 90 removably mounted in a battery holder 91 with output terminals 92. One of the terminals 92 serves to close the battery access opening 69 so that when the terminal 92 is removed, the battery 90 can be replaced as seen in FIG. 1. While different sizes of batteries with different voltages may be used, the particular battery illustrated is a type AA battery with a voltage output of 1.5 volts.

The control unit 65 will best be understood by reference to the electrical schematic seen in FIG. 8. The control unit 65 comprises generally a timed switching circuit 95 which intermittently connects the battery 90 to the drive motor 84 through a reversing switch 96 and also includes a flushing/return switch 98 which connects the battery 90 directly to the drive motor 84 through the reversing switch 96 bypassing the switching circuit 95. The timed switching circuit 95 comprises a variable oscillator 100 which controls an output switch 101 to connect and disconnect the motor 84 to the battery 90 through the flushing/return switch 98 and the reversing switch 96. The oscillator 100 has a variable RC timing circuit illustrated with a variable resistor $R_1$, a fixed resistor $R_2$ and a capacitor $C_1$. The output of the oscillator 100 controls the output switch 101, here shown as an NPN transistor with the output of the oscillator 100 connected to its base. The emitter of transistor switch 101 is connected to the positive side of the battery 90 while its collector is connected to the normally closed contact of flushing/return switch 98. The normally closed contact of switch 98 is also connected to the negative side of battery 90 through indicator lamp L. The normally open contact of flushing-/return switch 98 is connected directly to the positive side of battery 90. The flushing/return switch 98 is a microswitch with a switch lever 102 (FIGS. 1 and 7) while the reversing switch 96 is a double pole, double throw switch with a switch lever 104 (FIGS. 1 and 7). Switch 96 has a first set of contacts 105 and a second set of contacts 106 so that contact $105_1$ is closed when contact $106_1$ is closed while contact $105_2$ is closed when contact $106_2$ is closed. The common contact of the flushing/return switch 98 is connected to the contacts $105_1$ and $106_2$ while the contacts $105_2$ and $106_1$ are connected directly to the negative side of the battery 90. The common contact $105_c$ of switch 96 is connected to one side of motor 84 while the other common contact $106_c$ is connected to the other side of motor 84.

The output of the transistor switch 101 at its collector may be connected to the normally closed contact of the flushing/return switch 98 through a fusing device FD. The fusing device FD is sized so that the current flow therethrough during the time period of each injection pulse (i.e. motor 84 is running) is insufficient to burn out the fusing device FD but if the current flow is maintained through the fusing device FD for a significantly longer period of time (for instance, where control unit 65 fails with motor 84 continuously connected to battery 90), then the fusing device FD will burn out and disconnect motor 84 from battery 90 before injury to the patient occurs. It will be noted that the normally open contact of flushing/return switch 98 bypasses the fusing device FD so that it does not burn out when the flushing/return switch 98 is in use.

In operation, the output of oscillator 100 remains high while the capacitor $C_1$ is charging through the variable resistor $R_1$ and the resistor $R_2$. When the capacitor $C_1$ is charged to a prescribed voltage such as about 0.5 volt, the output of the oscillator 100 pulses low for a fixed time period while the capacitor $C_1$ is discharged. This causes the base of transistor switch 101 to also go low and the switch 101 to connect the battery 90 to the normally closed contact of flushing/return switch 98. This energizes the motor 84 and illuminates the lamp L to indicate visually that the motor 84 is operating to drive the expelling unit 61 to expel fluid F from the ampule 11. When the capacitor $C_1$ discharges to a prescribed lower level, the output of oscillator 100 goes low to cause the transistor switch 101 to disconnect motor 84 from battery 90 and stop motor 84 from expelling fluid F.

The time period that the output of the oscillator 100 remains high while capacitor $C_1$ is charging can be varied by changing the setting and thus the resistance of the variable resistor $R_1$. On the other hand, the motor 84 runs for a generally fixed period of time each time the base of transistor switch 101 is pulsed low. Thus, the overall injection rate of the fluid F can be varied by varying the resistance of resistor $R_1$ to change the number of low pulse outputs of oscillator 100. The length of time of each injection while motor 84 is running with the output of oscillator 100 low is limited by the variation permitted in the desired treatment fluid level in the patient since the intermittent injection of fluid F will inherently cause some variation in the fluid level in the patient. While different lengths of injection time may be used, good results have been obtained where the length of time of each injection output pulse from oscillator 100 was sufficient to cause about 6 units of treatment fluid F to be injected during each injection pulse. The flushing/return switch 98 connects the motor 84 directly to the positive side of the battery 90 so that the switching circuit 95 is bypassed when the normally open contact of switch 98 is closed. The reversing switch 96 reverses the rotation of motor 84 by reversing its connections to the battery 90.

It will be noted that the control access door 70 is a sliding door which, when opened, as seen in FIG. 1 exposes switch lever 104 of the reversing switch 96 and switch lever 102 of the flushing/return switch 98. Thus, when the control access door 70 is open in FIG. 1, the switch lever 102 on flushing/return switch 98 can be manually closed to cause the motor 84 to constantly drive the drive screw 76 to constantly force fluid out of the ampule 11 or to constantly retract the drive screw 76, depending on the position of the reversing switch 96. With the door 70 open, the switch lever 104 of the reversing switch 96 may also be manipulated to cause the motor 84 to either drive the drive screw 76 out of the housing 60 or into the housing 60. The switch lever 104 on the reversing switch 96 is located so that when the door 70 is closed as seen in FIG. 7, an abuttment 108 forces the switch arm 104 to its forward position so that the motor 84 is driven in the proper direction to cause the drive screw 76 to be forced out of the housing 60 and expel the fluid from the ampule 11. Further, a lockout member 109 is provided on the sliding door 70 so that when it is closed, switch lever 102 of the flushing/return switch 98 is prevented from being inadvertently closed to cause the motor 84 to go into its flushing operation.

To signal the patient and/or medical personnel when the piston 20 in ampule 11 bottoms out on rubber plug 16 to empty chamber 18 of fluid, a drive screw position switch PS may be provided as seen in FIG. 4. Thus, when the upper end of drive screw 76 clears the switch PS as the piston 20 bottoms out, the switch PS closes. As seen in FIG. 8 this activates an alarm AL to signal that ampule 11 is empty.

OPERATION OF FIRST EMBODIMENT

In operation, it will be seen that the injection device 10 will be assembled and usually portably supported on the patient so that the ambulatory capability of the patient is not limited. Generally, the ampule support and connector unit 12 and power unit 14 are shipped disassembled with the fluid ampules 11 being acquired in different varying quantities with different fluids depending on the ultimate use of the device 10. The ampule support and connector unit 12 is always maintained in a sterile condition, and preferably the drive screw 76 on power unit 14 is also in a sterile condition. Of course, the ampules 11 are always maintained in a sterile condition.

The dispensing and injecting device 10 is assembled by inserting the proper size ampule support 21 into the power unit 14 through opening 80 so that the support 21 is coaxial with screw axis $A_S$. Next, the fluid ampule 11 is inserted into the ampule support 21, it being noted that the ampule 11 can only be inserted into the ampule support 21 so that the rubber plug 16 is facing away from the drive screw 76. The housing 60 is also sized so that plug 16 on ampule 11 projects from the opening 81 to facilitate removal. The piercing cap assembly 22 is then screwed into place over ampule 11 so that the penetrable portion 19 of plug 16 will be penetrated by the piercing needle 40 to place the fluid F in ampule 11 in communication with the tubing DL. Usually, the battery 90 to be used is supplied from a conventional source and maintained separate from the power unit 14 until it is desired to use the device 10. The battery 90 is placed in the drive unit 14 by opening the battery access opening 69 and placing the battery in the battery holder 91 (see FIG. 1). The operator then watches to see if the control unit 65 times out to illuminate the lamp L to indicate that the control unit 65 is operating. If the battery is inadvertently reversed in the battery holder 91, the control unit 65 will not time out and the operator will then know that the battery has been reversed in the battery holder 91.

If the control unit 65 times out to momentarily illuminate the lamp L, then the operator raises the control access door 70 and manipulates the flushing switch lever 102 so that the motor 84 is continuously driven and the screw 76 is rotated to be axially extended to engage the piston 20 in the ampule 11 and start to force the fluid F from within the ampule 11 out into the tubing DL. When the tubing DL has been filled and the fluid F starts to come out of the injection needle assembly IN, the operator releases the switch lever 102 on the flushing/return switch 98 and the unit is now ready to be attached to the person. The injection needle assembly IN may be of the intravaneous injection type or the subcutaneous injection type depending on the particular fluid being injected and its use in the treatment.

The injection device 10 is conveniently attached to the patient as will be explained and the injection needle assembly IN is connected to the person. Because the control unit 65 drives the motor 84 for a prescribed period of time each time the control unit 65 energizes the motor 84, the injection rate can be easily monitored by checking the time period between the pulses of illumination of the lamp L. The variable resistance $R_1$ will usually be appropriately marked to give a gross injection rate reading and the operator then times the pulses of the lamp L and adjusts the variable resistance $R_1$ until the pulses reach the prescribed rate required for the desired injection rate. For instance, where the ampule 11 is sized to deliver 5 cc of fluid F for 3 cm of travel of the piston 20, where the control unit 65 drives the motor 1 revolution per pulse of the control unit 65, where the gear ratio of the transmission is 216:1, and where the drive screw 76 is arranged so that it moves about 1/32 inch (0.8 mm) per revolution, the control unit 65 will cause about 5 cc of fluid F to be injected in a 24 hour period if the motor is pulsed about 1 time every 10.6 seconds and the unit will deliver about 1 cc of fluid in a 24 hour period if the motor 84 is pulsed one time every 53 seconds. Thus, with a convenient chart provided with the device 10, the injection rate can be quickly and easily set. The device 10 will then continue to inject the fluid F at the prescribed rate. The patient and/or medical personnel can easily monitor the device 10 simply by first of all watching to see if the indicator lamp L periodically is illuminated and secondly can monitor the injection rate simply by timing the pulses on the indicator lamp L.

When it is necessary to replace the ampule 11, the piercing cap assembly 22 is disconnected from the power unit 14 and the used ampule 11 removed. A new ampule 11 can then be placed in the connector 21. At this time, it is necessary to return the drive screw 76 back to its initial position. This can be accomplished by raising the control access door 70 so that the switch lever 104 of the reversing switch 96 is released. The switch lever 104 can then be transferred to its reversing position and the switch lever 102 of the flushing/return switch 98 activated to continuously connect the motor 84 to the battery 90 so that the direction of rotation of the motor 84 is reversed and the drive screw 76 rotated in the opposite direction to retract the drive screw 76. When the drive screw 76 has been fully retracted, the switch lever 104 on the reversing switch 96 can then be returned to its forward position and the access door 70 closed. If the switch lever 104 is inadvertently left in its reversing position, the abuttment 108 will engage the switch lever 104 and return it to its forward position as the access door 70 is closed. Further, it will be noted that any time the access door 70 is closed, the lockout member 109 engages the switch lever 102 on the flushing/return switch 78 to prevent it from being activated. Once the access door 70 is closed, a new ampule 11 is inserted in support 21 and the piercing cap assembly 22 is attached back to the housing 60 on the power unit 14. It may be necessary to drive the screw 76 using the flushing/return switch 98 until it engages the piston 20 in the ampule 11. The operation of the device 10 is then repeated. Often times, it is necessary to change the injection rate while the device 10 is operating. This is easily and simply accomplished by changing the setting on the variable resistor $R_1$ until the desired pulse rate has been set.

SECOND EMBODIMENT

Referring to FIGS. 9–16, a second embodiment of the injection device is illustrated and is designated generally by the numeral 210. The injection device 210 uses the fluid ampule 11, an ampule connector 212, a power unit 214, and a piercing and metering unit 211. The ampule connector 212 mounts the ampule 11 on the power unit 214 so that the power unit 214 forces the fluid from the ampule 11 into the patient through the piercing and metering unit 211. Since the ampule 11 has been discussed in considerable detail with respect to the first embodiment of the invention, the detailed description thereof will be omitted from this portion of the specification and the same reference numbers applied to the first embodiment of the invention will be applied thereto.

Figure 12:
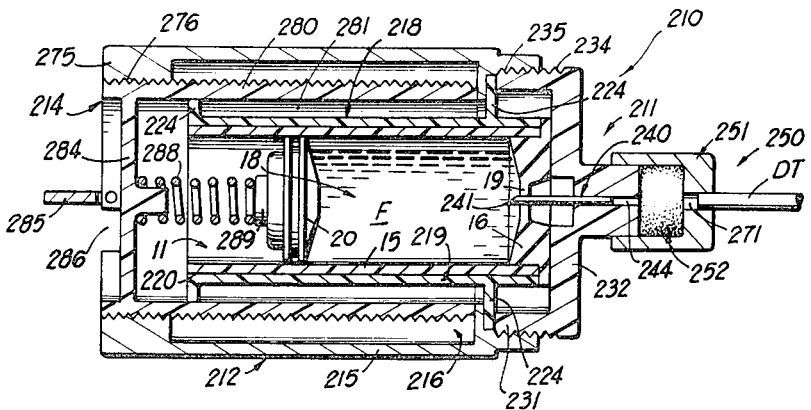
FIG. 12 is a view similar to FIG. 11 showing the invention in operation.
Figure 13:
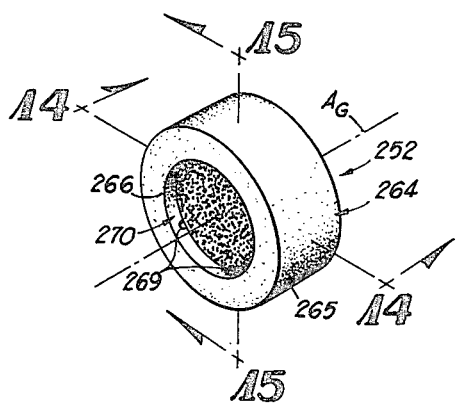
FIG. 13 is an enlarged perspective view of the metering assembly of FIGS. 9-12.

The ampule connector 212 is illustrated in FIGS. 11 and 12 as integral with the power unit 214, however, it is to be understood that the connector 212 may be made separable therefrom. The ampule connector 212 includes a generally cylindrical tubular side wall 215 integral with the power unit 214 at its inboard end to define a cylindrical chamber 216 therein of a prescribed diameter $d_c$.

An ampule adapter 218 is slidably received in chamber 216 at its distal end to support the ampule 11 similarly to the ampule support 21 for the first embodiment of the invention. It will thus be seen that a different size ampule adapter 218 would be used with different diameter ampules 11 as will become more apparent. The adapter 218 includes a cylindrical side wall 219 which defines an ampule receiving passage 220 therein just large enough to slidably receive the side wall 15 of ampule 11 therein as seen in FIGS. 11 and 12. An annular, outwardly projecting locating flange 224 is provided on adapter side wall 219 adjacent both the outboard and inboard ends thereof as seen in FIGS. 11 and 12. The flange 224 has an outside diameter which engages the side wall 215 of connector 212 to locate the adapter 218 as will become more apparent. It will be noted that the length of the adapter 218 is less than the length $L_A$ of the ampule 11 so that the rubber plug end of ampule 11 projects from the adapter 218 when it is in position as seen in FIGS. 11 and 12 as will become more apparent. The diameter of the inboard flange 224 on the inboard end of adapter 218 and the outside diameter of outboard flange 224 on the outboard end of adapter 218 are of a standard fixed size while the diameter of the ampule passage 220 may be varied for different diameter ampules 11. If the ampule 11 to be used will be of a fixed diameter, the adapter 218 may be built into the connector 212.

The piercing and metering unit 211 is adapted to be removably attached to the ampule connector 212 over the rubber plug end of the ampule 11 carried in the adapter 218. The piercing and metering unit 211 includes a cap 230 with a cylindrical tubular side wall 231 closed at its outboard end by a circular end wall 232 seen in FIGS. 11 and 12. The rubber plug end of ampule 11 is received through the inboard end of the cap side wall 231 until the rubber plug 16 is engaged by cap end wall 232 as seen in FIGS. 11 and 12. The inboard end of cap side wall 231 is provided with external threads 234 (FIG. 9) for engagement with internal threads 235 on the outboard end of connector side wall 215 to removably connect the cap 230 to the connector 212 as will become more apparent. The inside diameter of the cap side wall 231 is sized to receive the largest diameter ampule 11 to be used therein.

The cap end wall 232 mounts a tubular piercing needle 240 therein with a sharpened operating end 241 extending inboard of cap end wall 232 to pierce the penetrable plug 16 of the ampule 11. The needle 240 defines an outlet passage therethrough which opens onto the operating end of the needle 240. The opposite end of the needle passage communicates with a discharge passage 244 through the cap end wall 232 so that the fluid from the ampule 11 flowing through the needle 240 can flow out through the cap end wall 232 through the discharge passage 244. The needle 240 may be provided with a cover assembly 45 similar to the first embodiment of the invention to enhance the sterility thereof.

The metering assembly 250 seen in FIGS. 11–16 is connected to the cap 230 at the distal end or outboard end thereof so that the metering assembly 250 is in communication with the discharge passage 244 through which the fluid F is forced from the ampule 11. The metering assembly 250 serves to control the rate of flow of the fluid out of the ampule 11 as will become more apparent. The metering assembly 250 includes generally a positioning member 251 and a flow control assembly 252 which is carried by the positioning member 251 so that the flow control assembly 252 is in operative communication with the fluid from the discharge passage 244 in cap end wall 232.

The positioning member 251 illustrated includes a cylindrical side wall 254 which is closed at its outboard end by an end wall 255 to define a flow control chamber 256 therein which has a cylindrical shape, opens onto the near end of said wall 254 and is closed at the outboard end of the side wall 254 by the end wall 255. The near end of the side wall 254 may be internally threaded as indicated at 258 which threadedly engages external threads 259 formed on the outboard end of the end wall 232 of the cap 230. The outboard end surface 260 on the cap end wall 232 is generally normal to the injector axis $A_I$ and cooperates with the near inside surface 261 on the end wall 255 of the positioning member 251 to position the flow control assembly 252 in the flow control chamber 256 as will become more apparent.

The flow control assembly 252 seen in FIGS. 13–16 includes generally an incompressible porous member 262 which is carried in a compressible gasket 264. The porous member 262 is a disk shaped member with a thickness $t_{PM}$ and a diameter $d_{PM}$. The porous member 262 is commercially available as a ceramic filter where the flow rate through the porous member is linearly proportional to the pressure differential between the two sides of the porous member when the volume of the porous member exposed to the fluid is maintained substantially constant. By maintaining the incoming fluid pressure from the discharge passage 244 high relative to the much lower venous blood pressure on the downstream side of the porous member 262, the flow rate of the fluid through the porous member 262 can be accurately metered. The flow rate at a relatively constant pressure differential can be changed by varying the volume of the porous member 262 exposed to the fluid.

The compressible gasket 264 is made out of a resilient material such as rubber and includes a seamless cylindrical side wall 265 provided with inwardly directed seamless flanges 266 on the upstream and downstream ends thereof which are arranged generally normal to the gasket axis $A_G$. The seamless flanges 266 are spaced apart a prescribed distance $d_G$. The outside diameter $d_{OG}$ of the gasket side wall 265 is substantially equal to the inside diameter of the flow control chamber 256 in the positioning member 251 so that when the gasket 264 is positioned in the flow control chamber 256, the gasket 264 will be in sealing engagement with the side wall 254 of the positioning member 251 about the flow control chamber 256. The inside diameter $d_{IG}$ of the gasket 264 is about equal to the diameter $d_{PM}$ of the porous member 262. It will be also noted that the distance $d_G$ between the gasket flanges 266 is about equal to the thickness $t_{PM}$ of the porous member 262 so that the gasket side wall 265 and the seamless gasket flanges 266 define a porous member cavity 268 in the compressible gasket 264. Each of the seamless flanges 266 define an opening 270 therethrough of a diameter $d_{GO}$ smaller than the inside diameter $d_{IG}$ of the side wall 265.

Figure 14:
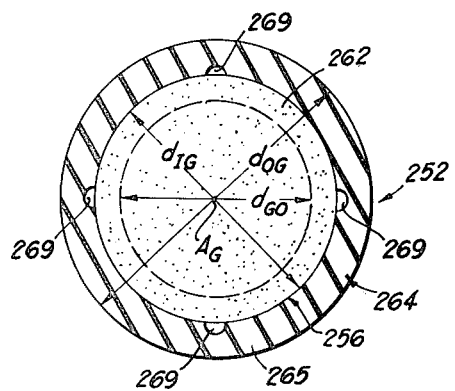
FIG. 14 is a transverse cross-sectional view taken along line 14—14 in FIG. 13.
Figure 15:
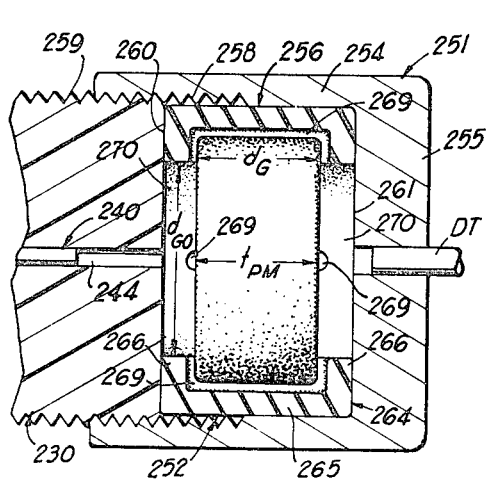
FIG. 15 is a longitudinal cross-sectional view taken along line 15—15 in FIGS. 13 and 14 showing the metering assembly in its flushing position.
Figure 16:
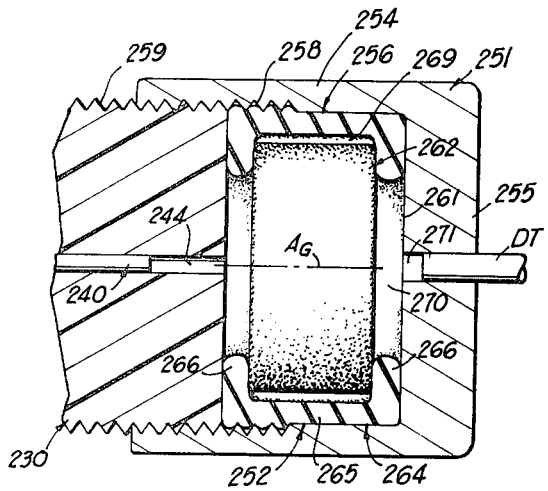
FIG. 16 is a view similar to FIG. 15 showing the metering assembly in its metering position.

Because the seamless flanges 266 are resilient, one of these flanges can be deformed so that the porous member 262 can be inserted into the porous member cavity 268 as seen in FIGS. 14 and 15. It will further be seen that the inside edges of the seamless gasket flanges 266 and the gasket side wall 265 are grooved as indicated at 269 at circumferentially spaced locations in the gasket 264. When the porous member 262 is positioned in the cavity 268, the grooves 269 provide passages around the edges of the porous member 262 so that fluid can flow around the edges of the porous member 262 in a generally unrestricted manner without having to pass through the porous member 262 at a controlled rate. This is permitted when the gasket 264 is carried in the flow control chamber 256 in an uncompressed state as seen in FIG. 15. When the positioning member 251 is screwed further onto the external threads 259 on the cap 230 to cause the gasket 264 to be compressed between the end wall 255 of the positioning member 251 and the cap end wall 232 on the cap 230, the seamless gasket flanges 266 on the compressible gasket 264 are deformed sufficiently to close the grooves 269 and seal the gasket flanges 266 to the porous member 262 so that the fluid can only flow through the porous member 262 whereby the flow rate of the fluid through the porous member 262 is accurately metered. This is seen in FIG. 16. It will further be noted that the effective flow rate through the porous member 262 can be changed by changing the diameter $d_{GO}$ of the openings 270 through the seamless gasket flanges 266 to change the volume of the porous member 262 exposed to the fluid.

An appropriate passage 271 is provided through the end wall 255 of the positioning member 251 so that fluid passing through or around the porous member 262 can flow out of the passage 271. The passage 271 communicates with appropriate delivery tubing DT which directs the fluid flowing through the porous member 262 to the point of injection into the patient through an appropriate injection needle assembly IN similar to the injection needle assembly IN for the first embodiment of the invention. Thus, it will be seen that the positioning member 251 is screwed down on the threads 259 on the cap 230 sufficiently to seal the flow control chamber 256 but insufficiently to collapse the grooves 269 so that the power unit 214 forces the fluid from the ampule 11 out through the grooves 269 to flush the tubing DT and the injection needle assembly IN and fill same with fluid. The positioning member 251 is then further screwed onto the cap threads 259 so that the gasket flanges 266 are deformed and the by-pass grooves 269 collapsed to prevent the flow of fluid through the grooves 269. At this point, the drive unit 214 then forces the fluid F from the ampule 11 through the porous member 262 so that the flow rate of the fluid to the patient is accurately metered.

Figure 17:
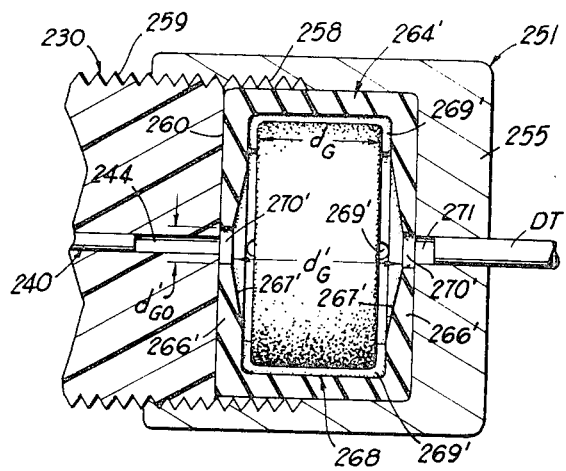
FIG. 17 is a view similar to FIG. 15 showing a modified metering assembly.

Referring to FIG. 17, a modification of the compressible gasket is illustrated and is designated 264'. The gasket 264' permits variations in the flow rate through the porous member 262 by changing the volume of the porous member 262 exposed to the fluid without having to change the diameter $d_{GO}'$ of the passage 270' through the gasket 264'. The outside diameter $d_{OG}$ and the inside diameter $d_{IG}$ of the gasket side wall 265' is the same as that of the gasket side wall 265. The distance $d_G$ between the gasket flanges 266' at their juncture with the side wall 265' is also the same as that for the gasket 264. It will be noted that the diameter $d_{GO}'$ of the openings 270' in gasket 264' is smaller than that of the openings 270 in the compression gasket 264. When the porous member 262 is positioned in the porous member cavity 268', grooves 269' provide the same flushing capability as the grooves 269 in the compression gasket 264. It will be noted that the inside surfaces 267' of the seamless gasket flanges 266' taper uniformly outwardly from the diameter $d_G$ to a diameter $d_G'$ as seen in FIG. 17 so that the seamless gasket flanges 266' are thinner at the inboard edge adjacent the opening 270' than at the outboard edge where they join with the gasket side wall 265'. It will thus be seen that the volume of the porous member 262 exposed to the fluid can be carried by further tightening the positioning member 251 to compress the flanges 266' so that more and more of the inside surfaces 267' of the seamless gasket flanges 266' are in contact with opposite faces of the porous member 262. Because the thickness $t_{PM}$ of the porous member 262 remains constant, the effective volume of the porous member 262 exposed to the fluid is varied by varying the cross-sectional area of the porous member 262 exposed to the fluid. Thus, it will be seen that maximum flow through the porous member 262 is permitted when the seamless gasket flanges 266' are compressed just sufficiently to seal the by-pass grooves 269' and permits a minimum flow rate when the seamless gasket flanges 266' are compressed sufficiently to cause the inside surfaces 267' to fully contact the opposite faces of the porous member 262.

The power unit 214 is integral with the inboard end of the ampule connector 212 and engages the piston 20 in the ampule 11 to force the fluid F from the ampule 11 using spring pressure. The power unit 214 includes generally a cap plate 275 which closes the inboard end of the chamber 216 in the connector side wall 215 as seen in FIGS. 11 and 12. The end plate 275 defines a central sleeve opening 276 therethrough which is internally threaded. An externally threaded load sleeve 280 is threadedly received through the sleeve opening 276. The load sleeve 280 defines a passage 281 therein that is sized to slidably fit over the inboard locating flange 224 on the ampule adapter 218.

The inboard end of sleeve 280 is closed by an end plate 284 which pivotally mounts a handle 285 thereon as seen in FIGS. 10-12. The outside of the cap plate 275 is recessed at 286 so that when the sleeve 280 has been fully screwed into the connector 212 as seen in FIG. 12, the handle 285 can be folded into the recess 286 to lock the sleeve 280 as seen in FIG. 10.

A drive spring 288 is mounted centrally on the end plate 284 within sleeve 280. The spring 288 has a drive plunger 289 on the outboard end thereof which will extend into the open end of ampule 11 to engage piston 20. In its uncompressed state, the spring 288 has a length about that of the sleeve 280. Thus, when the sleeve 280 is retracted as seen in FIG. 11, the ampule 11 can be loaded in connector 212 without loading piston 20. When the sleeve 280 is fully extended into the connector 212 as seen in FIG. 12, the spring 288 then loads piston 20 to force fluid out of ampule 11.

THIRD EMBODIMENT

Figure 18:
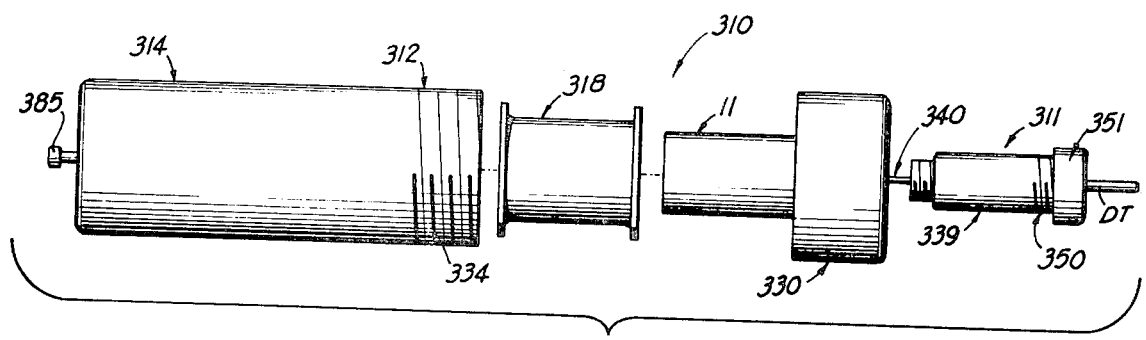
FIG. 18 is an exploded side view of a third embodiment of the invention.
Figure 19:
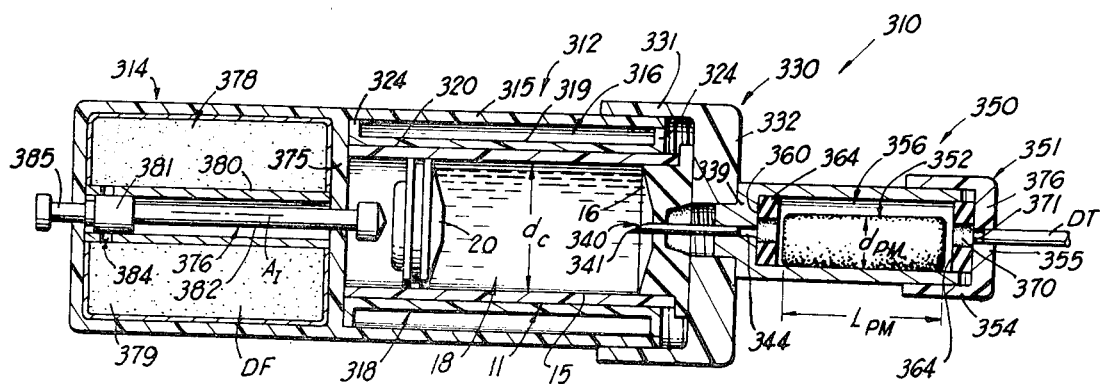
FIG. 19 is an enlarged longitudinal cross-sectional view of the invention of FIG. 18 showing the invention in its cocked position.

Referring to FIGS. 18-20, a third embodiment of the injection device is illustrated and is designated generally by the numeral 310. The injection device 310 uses the fluid ampule 11, an ampule connector 312, a power unit 314, and a piercing and metering unit 311. The ampule connector 312 mounts the ampule 11 on the power unit 314 so that the power unit 314 forces the fluid from the ampule 11 into the patient through the piercing and metering unit 311. Since the ampule 11 has been discussed in considerable detail with respect to the first embodiment of the invention, the detailed description thereof will be omitted from this portion of the specification and the same reference numbers applied to the first embodiment of the invention will be applied thereto.

The ampule connector 312 is illustrated in FIGS. 19 and 20 as integral with the power unit 314, however, it is to be understood that the connector 312 may be made separable therefrom. The ampule connector 312 includes a generally cylindrical tubular side wall 315 integral with the power unit 314 at its inboard end to define a cylindrical chamber 316 therein of a prescribed diameter $d_c$. The connector 312 also includes a cap 330 with a cylindrical tubular side wall 331 closed at its outboard end by a circular end wall 332 seen in FIGS. 19 and 20. The rubber plug end of ampule 11 is received through the inboard end of the cap side wall 331 until the rubber plug 16 is engaged by cap end wall 332 as seen in FIGS. 19 and 20. The inboard end of cap side wall 331 is provided with internal threads for engagement with the external threads 334 (FIG. 18) on the outboard end of the connector side wall 315 to removably connect the cap 330 to the connector side wall 315 as will become more apparent. The inside diameter of the cap side wall 331 is sized to receive the largest diameter ampule 11 to be used therein.

An ampule adapter 318 is slidably received in chamber 316 at its distal end to support the ampule 11 similarly to the ampule support 21 for the first embodiment of the invention. It will thus be seen that a different size ampule adapter 318 would be used with different diameter ampules 11 as will become more apparent. The adapter 318 includes a cylindrical side wall 319 which defines an ampule receiving passage 320 therein just large enough to slidably receive the side wall 15 of ampule 11 therein as seen in FIGS. 19 and 20. An annular, outwardly projecting locating flange 324 is provided on adapter side wall 319 adjacent both the outboard and inboard ends thereof as seen in FIGS. 19 and 20. The flanges 224 have outside diameters which engage the side wall 315 of connector 312 to locate the adapter 318 as will become more apparent. It will be noted that the length of the adapter 318 is less than the length $L_A$ of the ampule 11 so that the rubber plug end of ampule 11 projects from the adapter 318 when it is in position as seen in FIGS. 19 and 20 as will become more apparent. The diameter of the inboard flange 324 on the inboard end of adapter 318 and the outside diameter of outboard flange 324 on the outboard end of adapter 318 are of a standard fixed size while the diameter of the ampule passage 320 may be varied for different diameter ampules 11. If the ampule 11 to be used will be of a fixed diameter, the adapter 318 may be built into the connector 312.

The piercing and metering unit 311 is adapted to be removably attached to the end cap 330 of the ampule connector 312 over the rubber plug end of the ampule 11 carried in the adapter 318. The piercing and metering unit 311 includes a tubular piercing needle 340 carried by a holder 339 removably mounted in end wall 332 so that the sharpened operating end 341 of needle 340 projects into the cap 330 to pierce the rubber plug 16 on ampule 11. The needle 340 defines an outlet passage therethrough which opens onto the operating end 341 of the needle 340. The opposite end of the needle passage communicates with a discharge passage 344 through the holder 339 so that the fluid from the ampule 11 flowing through the needle 340 can flow out through the holder 339 through the discharge passage 344. The needle 340 may be provided with a cover assembly 45 similar to the first embodiment of the invention to enhance the sterility thereof.

The metering assembly 350 of the piercing and metering unit 311 seen in FIGS. 19 and 20 is connected to the holder 339 at the distal end or outboard end thereof so that the metering assembly 350 is in communication with the discharge passage 344 through which the fluid F is forced from the ampule 11. The metering assembly 350 serves to control the rate of flow of the fluid out of the ampule 11 as will become more apparent. The metering assembly 350 includes generally a positioning member 351 and a flow control assembly 352 which is carried by the positioning member 351 so that the flow control assembly 252 is in operative communication with the fluid from the discharge passage 344 in holder 339.

The positioning member 351 illustrated includes a cylindrical side wall 354 which is closed at its outboard end by an end wall 355. The holder 339 defines a flow control chamber 356 therein which has a cylindrical shape, opens onto the distal end of holder 339 and is closed at the inboard end of the holder 339. The near end of the side wall 354 is internally threaded which threadedly engages external threads formed on the outboard end of the holder 339. The end surface 360 on the holder 339 is generally normal to the injector axis $A_I$ and cooperates with the near inside surface 361 on the end wall 355 of the positioning member 351 to position the flow control assembly 352 in the flow control chamber 356 as will become more apparent.

The flow control assembly 352 seen in FIGS. 19 and 20 includes generally an incompressible solid cylindrical porous plug 362 which is carried in chamber 356 between a pair of compressible washers 364. The porous plug 362 has a length $L_{PM}$ and a diameter $d_{PM}$ and is commercially available as a ceramic filter where the flow rate through the porous member is linearly proportional to the pressure differential between the two sides of the porour member when the volume of the porous member exposed to the fluid is maintained substantially constant. By maintaining the incoming fluid pressure from the discharge passage 344 high relative to the much lower venous blood pressure on the downstream side of the porous member 362, the flow rate of the fluid through the porous member 362 can be accurately metered.

The compressible washers 364 are made out of a resilient material such as rubber and define an opening 370 therethrough of a diameter smaller than the diameter $d_{PM}$ of the porous member 362. Because the diameter $d_{PM}$ of porous member 362 is smaller than that of chamber 356, the positioning member 351 is screwed onto holder 339 as seen in FIG. 19 just sufficiently to seal chamber 356 but not compress washers 364. This allows the unit to be flushed since the fluid can flow around plug 362 in a generally unrestricted manner. When the positioning member 351 is screwed further onto the holder 339 as seen in FIG. 20 to cause the washers 364 to be compressed between the end wall 355 of the positioning member 351 and the holder 339, the washers 364 seal the ends of plug 362 so that the fluid can only flow through the porous plug 362 whereby the flow rate of the fluid through the porous plug 362 is accurately metered. It will further be noted that the effective flow rate through the porous plug 362 can be changed by changing the length of plug 362.

An appropriate passage 371 is provided through the end wall 355 of the positioning member 351 so that fluid passing through or around the porous plug 362 can flow out the passage 371. The passage 371 communicates with appropriate delivery tubing DT which directs the fluid flowing through the porous plug 362 to the point of injection into the patient through an appropriate injection needle assembly similar to the injection needle assembly IN for the first embodiment of the invention.

The power unit 314 is integral with the inboard end of the ampule connector 312 and engages the piston 20 in the ampule 11 to force the fluid F from the ampule 11 using fluid pressure. The power unit 314 includes generally a cap plate 375 which closes the inboard end of the chamber 316 in the connector side wall 315 as seen in FIGS. 19 and 20. The end plate 375 slidably mounts a drive unit 376 therein that is urged out of the plate 375 by a fluid pressure source 378 so that the fluid pressure source 378 can force the drive unit 376 into engagement with the drive piston 20 in ampule 11 to force the fluid F out through the piercing needle 340 and the discharge passage 344. The fluid pressure source 378 includes a pressure chamber 379 which contains a drive fluid DF under pressure with the pressure chamber 379.

The drive unit 376 includes a cylinder 380 which slidably mounts a piston 381 therein with a piston rod 382 connected to the piston 381 to be selectively extended and retracted into the cylinder 380 as the piston 381 is moved into the cylinder. The pressure chamber 379 is connected to the cylinder 380 through inlet ports 384 which are covered by the piston 381 when the piston rod is fully retracted as seen in FIG. 19. Thus, when the piston rod 382 is fully retracted, the piston 381 blocks ports 384 to prevent the drive fluid DF from entering the cylinder 380 to extend the piston rod 382 by driving the piston 381. A manual activating member 385 is attached to the cylinder 380 so that when the activating member 385 is pressed, the piston 381 will be displaced off of the inlet port 384 so that the drive fluid DF can enter the cylinder 380 through the inlet port 384 to force the piston 381 away from the port 384 and extend the piston rod 382. In this position, the drive fluid DF constantly urges the distal end of the piston rod 382 into engagement with the piston 20 in the ampule 11 to force the fluid F out of the ampule 11 as seen in FIG. 20. Once the ampule 11 has been emptied, the cap 330 on the ampule connector 212 can be removed and the piston rod 382 manually forced back to its retracted position in the cylinder 380 to force the drive fluid DF back into chamber 379 and the piston 381 once again covers the outlet port 384. The piston 381 and piston rod 382 will then remain in its retracted position until the activating member 385 is again pushed to reconnect the drive fluid DF to the piston 381 to extend the piston rod 382.

SUPPORT HARNESS AND MANIFOLD

A support harness assembly 400 is illustrated in FIGS. 21 and 22 to conveniently attach the injection devices 10, 210 and/or 310 on the patient so that the portability of the invention does not restrict the ambulatory capability of the patient. The support harness 400 includes a wide elastic band 401 which confortably fits over the patient's arm without significantly affecting the patient's blood circulation. A first support pouch 402 is mounted thereon which defines a continuous injector pocket therein to receive the injection device 10 therein. The continuous pocket is closed by a flap 405 with an appropriate mechanism such as Velcro strips to hold the flap closed. A cutout 408 is provided in flap 405 to allow the lamp L to be visually monitored and an appropriate opening is provided so that the tubing DT and cap 30 from the device 10 can pass out of the pocket as seen in FIG. 22. A second pouch 410 is also mounted on band 401 with an intermittent injector pocket to receive the injection device 210 or 310 and is closed with a flap 412. An appropriate opening is provided for the tubing DT to pass therefrom. Hold-down straps 414 may be provided as seen in FIG. 22 to captivate any excess length of the tubing.

So that only one injection needle assembly IV need to be connected to the patient, a manifold block 420 may be provided as seen in FIGS. 21-24. This allows the fluid outputs from both devices 10, 210 and/or 310 to be combined as well as providing a convenient means to inject other fluids to the patient. The manifold block 420 may be permanently or removably attached to the band 401. Block 420 has a common delivery tube CDT therefrom to which is connected a common injection needle assembly IV for connection to the patient.

Figure 23:
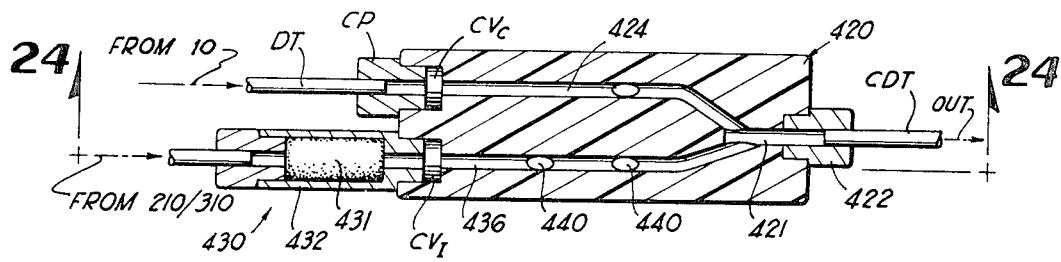
FIG. 23 is a longitudinal cross-sectional view of the manifold block seen in FIG. 22; and, FIG. 24 is a cross-sectional view taken along line 24—24 in FIG. 23.

The common delivery tube CDT is in communication with a common delivery chamber 421 in block 420 through a quick disconnect 422 seen in FIG. 23. The male coupling CP in the delivery tubing DT from the injection device 10 is connected to a continuous injection transfer chamber 424 through a check valve $CV_c$ and chamber 424 is connected to the delivery chamber 421 so that the fluid flows through the chamber 424 into delivery chamber 421 and then into the patient via tube CDT.

Figure 24:
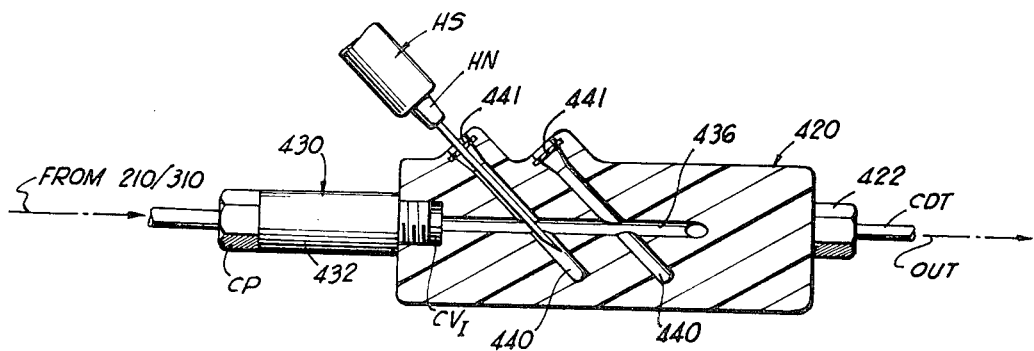

The metering assembly associated with devices 210 or 310 may be replaced by a metering assembly 430 connected to block 420 as seen in FIGS. 23 and 24. The metering assembly 430 includes a porous plug 431 sealed in a quick disconnect housing 432 so that fluid entering through the inlet end of housing 432 must flow through the porous plug 431 to the discharge end of housing 432. The discharge end of housing 432 is removably connected to delivery chamber 421 through transfer chamber 436 with an appropriate check valve $CV_I$ while the inlet end of housing 432 is connected to the coupling CP in delivery tubing DT from device 210 or 310 without metering. If it is necessary to flush the transfer chamber 436 and delivery chamber 421 when using devices 210 or 310 with metering assembly 430, the assembly 430 is removed from chamber 436 and the coupling CP screwed directly into the chamber 436 until flushing is completed. Then, the coupling CP and metering assembly 430 are reattached as seen in FIGS. 23 and 24.

It is also frequently desirable to provide short injections of medication to the patient with needle devices such as the hypodermic syringe HS partly seen in FIG. 24. To accommodate these injections, the manifold block 420 is provided with cross chambers 440 best seen in FIG. 24. The cross chambers 440 intersect one of the chambers 421, 424 or 436 and each are provided with a penetrable plug 441 (FIG. 24) such as rubber so that the needle HN on the syringe HS can be inserted through plug 441 to one of the cross chambers 440. The syringe HS can then be used to inject unmetered fluid into the patient via the common delivery tubing CDT. Because the block 420 is made out of a strong material, the needle HN will not penetrate same to prevent the injection and also isolates the needle HS from the delivery tubing CDT.

So that the fluid level in the ampule 11 can be visually monitored, the side wall 15 will usually be made out of a clear material. The ampule support 21 for device 10, the ampule adapter 218 for device 210, and the ampule adapter 318 for device 310 will also usually be clear or transparent. The housing 60 may be transparent or provided with a viewing window AW shown by phantom lines in FIG. 1 to facilitate this visual checking. The devices 210 or 310 would be similarly provided. The pouches 402 and 410 would likewise be provided with openings or windows VW as seen in FIG. 22.

While specific embodiments of the invention have been disclosed herein, it is to be understood that full use may be made of modifications, substitutions and equivalents without departing from the scope of the inventive concept as disclosed herein.

What is claimed as invention is:

1. An injector to inject fluid into a patient comprising:
    an ampule holder defining an ampule receiving chamber therein;
    an ampule assembly removably mounted in said ampule receiving chamber in said ampule holder, said ampule assembly including an ampule comprising:
        a seamless tubular side wall defining a passage therethrough opening onto opposite ends of said side wall;
        a penetrable member closing one end of said passage at one end of said side wall so that a discharge opening from said passage can be made by penetrating said penetrable member; and
        a piston member slidably received in said passage from that end of said tubular side wall opposite said penetrable member and in sealing engagement with said tubular side wall so that a fluid chamber is defined by and between said tubular side wall, said piston member and said penetrable member and filled with the fluid whereby the fluid can be dispensed from said fluid chamber upon penetration of said penetrable member to form the discharge opening and forcing said piston member toward said penetrable member;
    cap means removably connected to said ampule holder and engaging that end of said ampule at said penetrable member to positively and removably position said ampule in said ampule receiving chamber;
    penetrating means carried by said cap means for penetrating said penetrable member on said ampule as an incident to the positioning of said ampule in said ampule holder and for forming a fluid outlet from said fluid chamber through which the fluid is injected into the patient;
    a manually engagable externally threaded sleeve member having a projecting end and an opposite end and defining an axially extending ampule receiving passage therein; said sleeve member threadedly engaging said ampule holder so that, as said sleeve member is screwed into said ampule holder, the projecting end of said sleeve member is moved axially along said ampule receiving chamber in said ampule holder and that end of said ampule opposite said penetrable member is slidably supported by said sleeve member within said ampule receiving passage therein, said sleeve member including an end wall at said opposite end closing said ampule receiving passage; and
    a drive spring assembly extending between said end wall on said sleeve member and said piston, said drive spring assembly including a compressible coil spring mounted on said end wall of said sleeve member and having a projecting end extending axially of said sleeve member within said ampule receiving passage toward said piston, said drive spring assembly further including a drive plunger on the projecting end of said coil spring operatively engaging said piston so that, as said coil spring is compressed, the spring force urges said piston toward said penetrable member to force fluid out the fluid outlet, the length of said coil spring selected so that, as said sleeve member is manually screwed into said ampule holder, the compression of said coil spring is increased to selectively increase the effective spring force urging said piston toward said penetrable member.

2. The injector of claim 1 further including:
    an ampule adapter defining an ampule passage therein centered in said adapter and sized to slidably receive said side wall of said ampule therein to maintain said ampule centered in said ampule adapter; said ampule adapter slidably received in said chamber in said ampule holder, and including first locating means at one end of said ampule adapter to maintain one end of said ampule adapter coaxially centered in said chamber in said ampule holder and second locating means at the opposite end of said ampule adapter to maintain said opposite end of said ampule adapter coaxially centered in said chamber in said ampule holder to coaxially center said ampule in said ampule receiving chamber in said ampule holder.

3. The injector of claim 1 wherein said penetrating means further includes a piercing needle assembly having a sharpened piercing point thereon coaxially extending into said ampule receiving chamber of said ampule holder to penetrate said penetrable member of said ampule when said ampule is carried in said ampule receiving chamber of said ampule holder to form said fluid outlet from said fluid chamber in said ampule through said piercing needle assembly.

4. The injector of claim 3 further including a cover assembly for enhancing the sterility of said piercing needle comprising:

a penetrable cover member capable of being penetrated by the piercing point on said piercing needle;

positioning means for selectively positioning said penetrable cover member in alignment with the piercing point of said piercing needle so that said penetrable cover member is movable axially of said piercing needle from a non-use position in which the piercing point of said piercing needle is enclosed by said positioning means and said penetrable cover member to a use position in which the piercing point of said piercing needle is exposed by penetrating the penetrable cover member; and urging means for urging said penetrable cover member toward its non-use position.

5. The injector of claim 1 further including metering means operatively connected to said piercing means to regulate the flow of fluid from said ampule.

6. The injector of claim 5 wherein said metering means includes a porous member for regulating the flow of the fluid from said ampule and gasket means operatively connecting said porous member to said penetrating means, said gasket means having a first flushing position in which the fluid from said ampule is allowed to bypass said porous member without regulation and a second metering position in which the fluid from said ampule must pass through said porous member to regulate the flow thereof from said ampule.

* * * * *